(12) United States Patent
Cameron et al.

(10) Patent No.: US 6,469,190 B2
(45) Date of Patent: Oct. 22, 2002

(54) ALUMINUM COMPOUNDS FOR PRODUCING VINYLIC POLYMERS

(75) Inventors: Paul Alexander Cameron, Northallerton; Vernon Charles Gibson, London; Derek John Irvine, Cleveland, all of (GB)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 09/750,220

(22) Filed: Dec. 29, 2000

(65) Prior Publication Data

US 2001/0016637 A1 Aug. 23, 2001

Related U.S. Application Data

(63) Continuation of application No. PCT/GB99/01771, filed on Jun. 4, 1999.

(51) Int. Cl.$^7$ .................................................. C07F 5/06
(52) U.S. Cl. ...................................................... 556/175
(58) Field of Search .......................................... 556/175

(56) References Cited

PUBLICATIONS

Atwood, David A. et al., "Cationic Aluminum Compounds with Potential Relevance to Lewis Acid Catalysis", J. Am, Chem. Soc. (1995), 117(25), pp. 6779–6780.

*Primary Examiner*—Mark L. Berch
*Assistant Examiner*—Kahsay Habte
(74) *Attorney, Agent, or Firm*—Pillsbury Winthrop LLP

(57) ABSTRACT

An enolate functionalized reaction intermediate, represented by the formula (I) shown in the specification, such as, N,N'-ethylenebis (3,5-di-tertbutylsalicylidene imine) enolate of ter-butyl-isobutyrate aluminum, is useful for the production of vinyl polymers, such as polymethylmethacrylate, from the corresponding vinyl polymers, e.g., methylmethacrylate, by a living polymerization reaction. A Lewis acid may be used in the polymerization.

3 Claims, 1 Drawing Sheet

NMR of Enolate Reaction Intermediate

ALUMINUM COMPOUNDS FOR PRODUCING VINYLIC POLYMERS

Figure 1:
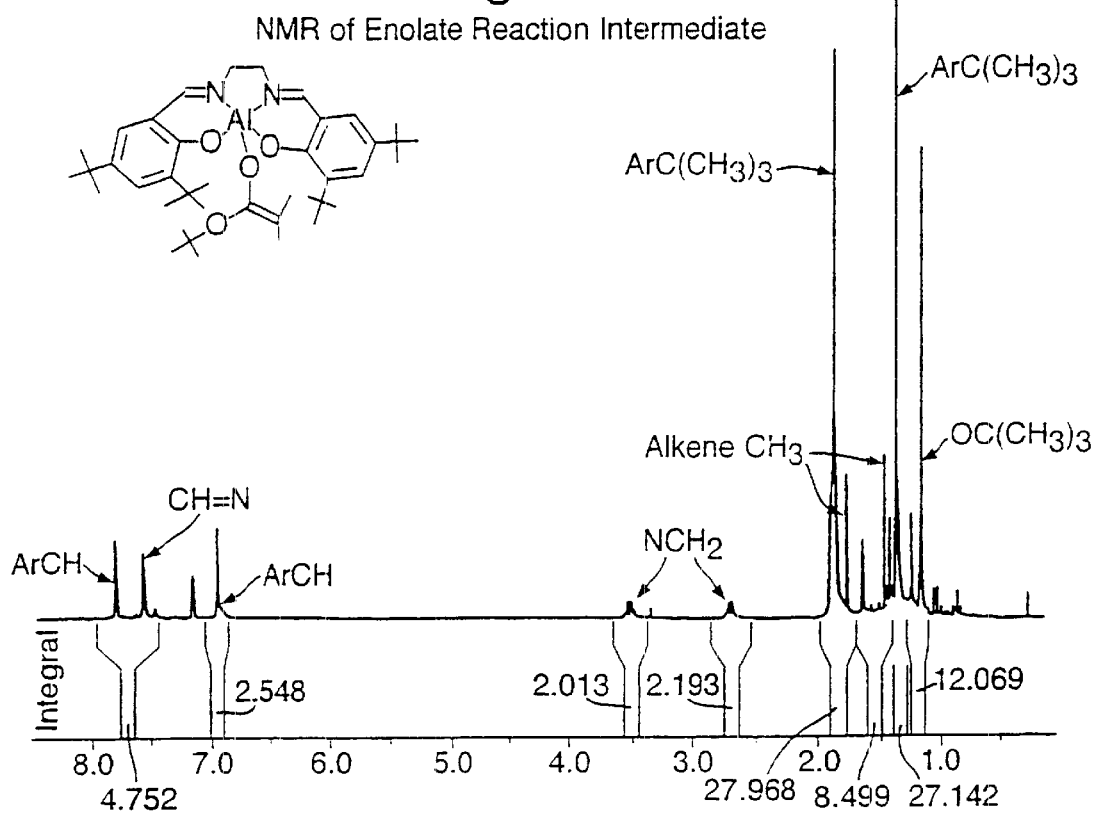

This application is a continuation of application Ser. No. PCT/GB99/01771, filed Jun. 4, 1999.

A Compound

The present invention relates to an enolate functionalised reaction intermediate, a method for its preparation and a vinylic polymer produced from reaction of said enolate functionalised reaction intermediate with vinylic monomer. Living or immortal polymerisation is a type of polymerisation that does not terminate naturally. Each initiator molecule produces one growing chain such that the polymer grows linearly with time. Therefore the degree of polymerisation can be controlled to some extent. This method has been developed by Inoue for the living polymerisation of both methacrylates and acrylates using aluminium porphyrins, of the general formula (TPP)AlX, as initiators with irradiation from a xenon arc (Polym. Prepr. Jpn. (English Edition) 1992, 41, E93(IIID-06) and E96(IIID-12).

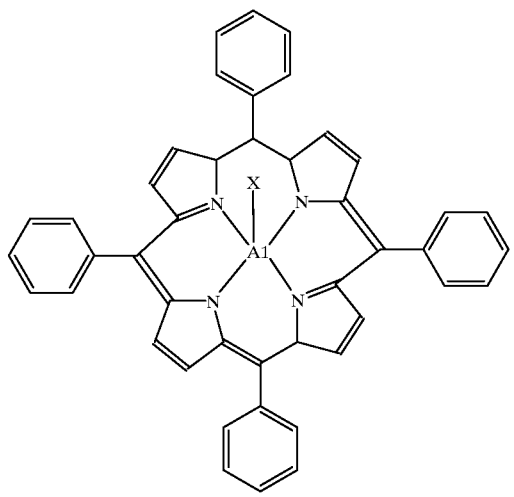

(TPP)AlX where X=$CH_3$ or $SCH_2CH_2CH_3$

At ambient temperature each (TPP)AlX molecule was found to generate a polymer chain and excellent control of molecular weight was achieved.

Subsequently Inoue discovered that the further addition of a Lewis acid greatly enhances the rate of propagation. For example (TPP)AlMe initiated polymerisation of methylmethacrylate (MMA), in the presence of irradiated light, was found to yield 6.1% polymethylmethacrylate after 2.5 hours. With the addition of a Lewis acid, for example a bulky aluminium phenoxide, there was quantitative polymerisation within 3 seconds. More recently Inoue has disclosed such systems where the presence of irradiated light is not required. For example (TPP)AlX, where X=SPropyl, initiated polymerisation of MMA in the presence of a Lewis acid, where there is complete monomer conversion after 1.5 minutes at 80° C. (T. Kodeira and K. Mori, Makromol. Chem. Rapid Commun. 1990, 11, 645). However the molecular weights that have been produced with this system have been low, for example 22,000.

It is reported, by Inoue, that the initial reaction is of the (TPP)AlX complex with monomer to form an enolate initiator as the reaction intermediate, in the presence of irradiated light. This enolate can then react with further monomer in the presence of the Lewis acid to develop the polymer chain.

It is an object of the present invention to provide an enolate functionalised reaction intermediate, a method for its preparation and a vinylic polymer produced from reaction of said enolate functionalised reaction intermediate with vinylic monomer.

Accordingly in a first aspect the present invention provides an enolate functionalised reaction intermediate of general formula (I)

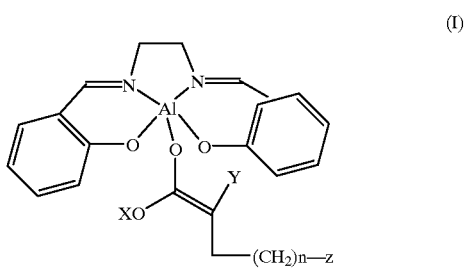

wherein X is an alkyl group; Z is selected from the group consisting of alkyl, hydrogen, halogen, alkoxy, thiol, aryloxy or ester; n is an integer and includes n=0; Y is alkyl or H; the tetradentate ligand around the Al is optionally substituted In a second aspect, the present invention provides a process for the preparation of an enolate functionalised reaction intermediate of general formula (I) wherein X is an alkyl group; Z is selected from the group consisting of alkyl, hydrogen, halogen, alkoxy, thiol, aryloxy or ester; n is an integer and includes n=0; Y is alkyl or H, the tetradentate ligand around the Al is optionally substituted which process comprises the steps of (i) Preparing a metal complex of general formula (II),

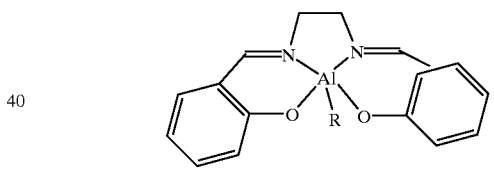

where R is a leaving group, in a solvent (ii) Preparing a metal enolate of a monomer, selected from the group consisting of (alk)acrylic acids or alkyl esters thereof, in a second solvent (iii) Mixing the two solutions of (i) and (ii) together (iv) Isolating the enolate functionalised reaction intermediate In a third aspect the present invention provides a vinylic polymer which is prepared from the reaction of an enolate functionalised reaction intermediate of general formula (I) with a vinylic monomer and a Lewis acid of general formula (III)

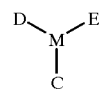

wherein at least one of C, D or E is capable of forming a coordination bond with Al of the enolate functionalised reaction intermediate, the others of C, D or E are bulky groups and M is selected from the group consisting of aluminium, magnesium, zinc and boron.

In the enolate functionalised reaction intermediate (I) X is preferably an alkyl group ranging from $C_1$–$C_{20}$. For Z by thiol we mean both SH and $SR^1$ groupings where $R^1$ includes alkyl, ester, ether. Z is preferably alkyl or hydrogen. Where Z may be alkyl it is preferably $C_1$–$C_8$ alkyl, more preferably methyl. n is preferably in the range 1 to 10, more preferably 1 to 5. When Y is an alkyl group it is preferably $C_1$–$C_{20}$, more preferably $C_1$–$C_4$. Optional substitution is preferably on the two aromatic rings of the tetradentate ligand around Al, more preferably substitution is of two tertiary butyl groups on each of these two aromatic rings.

In the process of the present invention the metal complex is of a general formula (II) where R is preferably chosen from the group consisting of alkyl, halogen, alkoxy, thiol, aryloxy or ester. The tetradentate ligand around the Al may be optionally substituted. Optional substitution is preferably on the two aromatic rings of the tetradentate ligand around the Al, more preferably the substitution is of two tertiary butyl groups on each of these two aromatic rings. Preferably the ratio of number of moles of metal complex (II) to moles of the metal enolate of a monomer, selected from the group consisting of (alk)acrylic acids or alkyl esters thereof is 1:1.

In the third aspect of the invention the bulky groupings in the Lewis acid (III) are preferably the same, in particular phenoxide or a substituted phenoxide or thiolate; The one of C, D or E which is capable of forming a co-ordination bond with the Al of the enolate functionalised reaction intermediate is preferably chosen from the group consisting of alkyl, halogen, alkoxy, aryloxy and ester, more preferably it is an alkyl group and more specifically methyl. M is preferably aluminium.

The vinylic polymers that can be produced according to this invention include homo and copolymers of the corresponding vinylic monomers such as alkyl (alk)acrylic acid and esters thereof, functionalised alkyl(alk)acrylic acid and esters thereof, for example hydroxy, halogen, amine functionalised, styrene, vinyl acetates, butadiene, olefins or olefinic oxides. By (alk)acrylic, we mean that either the alkacrylic or the analogous acrylic may be used. For both homo and copolymers the monomers are preferably alkyl (alk)acrylic acid and esters thereof, more preferably alkyl (meth)acrylates. These polymerisations can be conducted in such a way that architectural copolymers, for example block, ABA and stars, can be produced.

For both homo and copolymers the monomers are preferably alkyl (meth)acrylates. The ratio of number of moles of vinylic monomer to moles of enolate functionalised reaction intermediate is preferably from 1:1 to 20000:1. The ratio of the number of moles of enolate functionalised reaction intermediate to number of moles of Lewis acid preferably ranges from 1:0.1 to 1:100, more preferably from 1:0.2 to 1:10.

Polymerisation can be undertaken in the presence of a solvent, for example toluene, dichloromethane and tetrahydrofuran, or in the bulk monomer. The polymerisation is preferably undertaken at between −100 and 150° C., more preferably between −50 and 50° C., in particular between 15 to 40° C. The present invention is illustrated by reference to the following examples.

EXAMPLE 1

Preparation of N,N' ethylenebis (3,5-di-tertbutylsalicylidene imine)

A solution of 3,5-di-tert-butylsalicylaldehyde (3 g, 12.8 mmol) in ethanol (150 ml) was prepared. To this ethylene diamine (0.43 ml, 6.4 mmol) was added via syringe with stirring. The solution was heated to reflux for 15 minutes then allowed to cool to room temperature to allow crystals of N,N' ethylenebis (3,5-di-tertbutylsalicylidene imine) to develop. These were isolated by filtration.

EXAMPLE 2

Preparation of N,N' ethylenebis (3,5-di-tertbutylsalicylidene imine) chloro aluminium (Compound of general formula (II))

A solution of dimethylatuminium chloride in toluene (6.1 ml, 6.1mmol) was added dropwise to a solution of N,N' ethylenebis (3,5-di-tertbutylsalicylidene imine) (3 g, 6.1 mmol) in toluene (40 ml). The product precipitated out of solution. The suspension was further stirred for 12 hours and the liquor removed to leave a powdery solid of N, N' ethylenebis (3,5-di-tertbutylsalicylidene imine) chloro aluminium.

EXAMPLE 3

Preparation of lithium enolate of tert- butyl-isobutyrate n-butyllithium (1.6M in hexane, 1.13 ml, 1.18 mmol) was added dropwise at −78° C. over 15 mins to a solution of diisopropylamine (0.25 ml, 1.81 mmol) in diethylether (20 ml). The resulting solution was added dropwise at −78° C. over 5 mins to a solution of tert-butyl-isobutyrate (0.32 ml, 1.81 mmol) in diethylether (20 ml) to form the lithium enolate of tert-butyl-isobutyrate.

EXAMPLE 4

Preparation of N, N' ethylenebis (3,5-di-tertbutylsalicylidene imine) enolate of tert-butyl -isobutyrate aluminium (compound of general formula (I))

The solution of lithium enolate of tert-butyl -isobutyrate, as prepared in Example 3, was added dropwise to a solution of N, N' ethylenebis (3,5-di-tertbutylsalicylidene imine) chloro aluminium (1 g, 1.81 mmol), as prepared in Example 2, in tetrahydrofuran (50 ml) at −78° C. The reaction solution was allowed to warm to ambient temperature and stirred for 12 hours. The volatiles were removed by vacuum and the product extracted into pentane (10 ml), filtered and allowed to crystallise as a yellow-orange microcrystalline solid.

Figure 2:
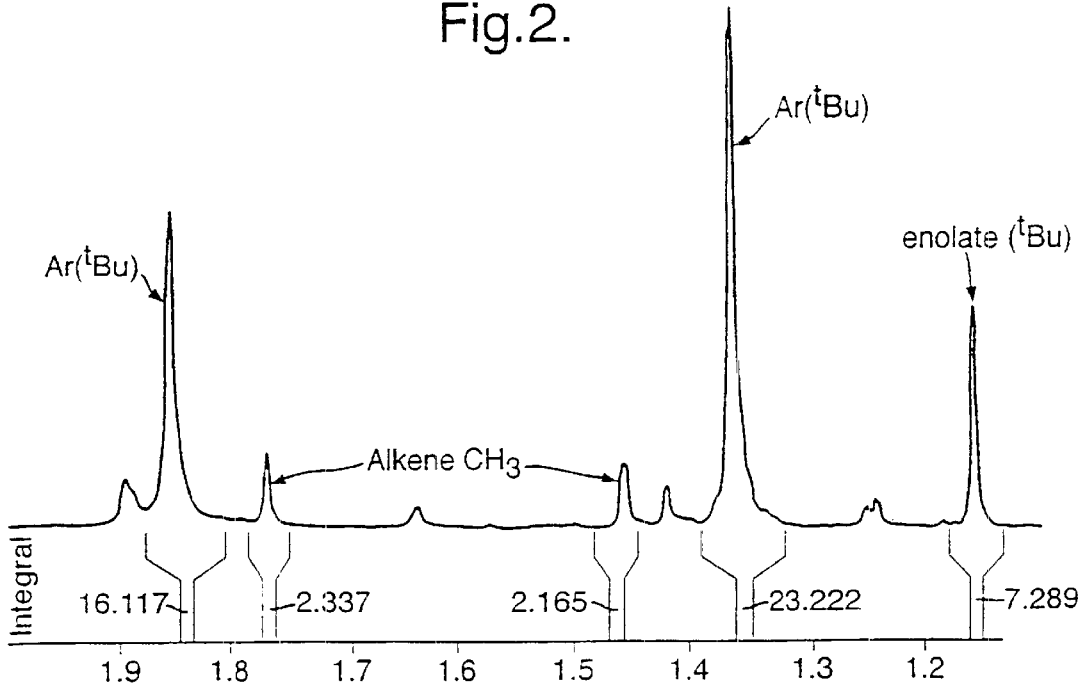

The structure was confirmed by $^1$H NMR at 250 MHz on a Bruker AC-250 machine as shown in FIGS. 1 and 2.

EXAMPLE 5

Preparation of Polymethylmethacrylate (PMMA)

A solution of methylmethacrylate (MMA) (1 g) in toluene (2 ml) was prepared in a flask under nitrogen. Into a second flask N, N' ethylenebis (3,5-di-tertbutylsalicylidene imine) enolate of tert-butyl -isobutyrate aluminium, as prepared in Example 4, (33.4 mg, 0.05 mmol) and methylaluminium bis (2,6-di-tert-butyl-4-methylphenoxide) (72.0 mg, 0.15 mmol) were added. The solutions of both flasks were mixed and stirred for 5 mins. Methanol (0.5 ml) was added to quench the reaction followed by toluene (2 ml). The PMMA was precipitated on addition to a 10 fold excess of acidified (1% concentrated hydrochloric acid) methanol. It was then isolated by filtration. The yield was 90.1% of PMMA.

The PMMA polymer had an actual molecular weight of 32,700 compared to the calculated value of 20,000. The polydispersity was 1.10 and the percentage syndiotacticity was 74%.

What is claimed is:

1. An enolate functionalized reaction intermediate of formula (I)

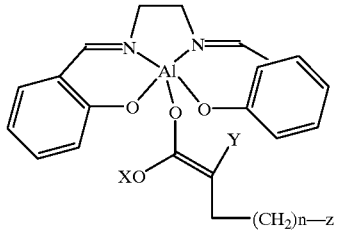

wherein X is an alkyl group; Z is selected from the group consisting of alkyl, hydrogen, halogen, alkoxy, SH, SR', where R' is alkyl, and aryloxy; n=0–10; Y is alkyl or H; the tetradentate ligand around the Al is optionally substituted with alkyl groups on each of the aromatic rings.

2. An enolate functionalised reaction intermediate as claimed in claim 1 wherein Z is $C_1$ to $C_8$ alkyl or hydrogen.

3. An enolate functionalized reaction intermediate of formula (I)

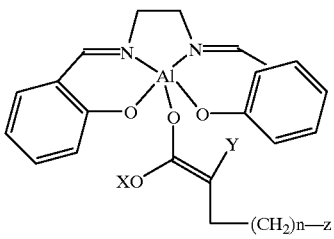

wherein X is an alkyl group; Z is selected from the group consisting of alkyl, hydrogen, halogen, alkoxy, SH, SR', where R' is alkyl, and aryloxy; n=0–10; Y is alkyl or H; the tetradentate ligand around the Al is substituted with two tertiary butyl groups on each of the aromatic rings.

* * * * *